US009638672B2

United States Patent
Butera, III et al.

(10) Patent No.: US 9,638,672 B2
(45) Date of Patent: May 2, 2017

(54) SYSTEM AND METHOD FOR ACQUIRING ACOUSTIC INFORMATION FROM A RESONATING BODY

(71) Applicants: Joseph G. Butera, III, Stuart, FL (US); Ryan J. Copt, Port St. Lucie, FL (US); Robert J. Summers, III, Port St. Lucie, FL (US)

(72) Inventors: Joseph G. Butera, III, Stuart, FL (US); Ryan J. Copt, Port St. Lucie, FL (US); Robert J. Summers, III, Port St. Lucie, FL (US)

(73) Assignee: Bongiovi Acoustics LLC, Port St. Lucie, FL (US)

( * ) Notice: Subject to any disclaimer, the term of this patent is extended or adjusted under 35 U.S.C. 154(b) by 0 days.

(21) Appl. No.: 14/640,665

(22) Filed: Mar. 6, 2015

(65) Prior Publication Data

US 2016/0258907 A1 Sep. 8, 2016

(51) Int. Cl.
*A61B 7/04* (2006.01)
*G01N 29/24* (2006.01)
(Continued)

(52) U.S. Cl.
CPC ............ *G01N 29/2418* (2013.01); *G01H 9/00* (2013.01); *G01N 29/14* (2013.01); *H04R 23/008* (2013.01)

(58) Field of Classification Search
CPC ............ H04R 23/008; H04R 2201/003; H04R 2227/003; H04R 2499/11; H04R 27/00; H04R 3/005; H04R 5/04; H04R 1/08; H04R 1/083; H04R 1/225; H04R 1/342; H04R 1/406; H04R 2201/107; H04M 1/72572;
(Continued)

(56) References Cited

U.S. PATENT DOCUMENTS 3,795,876 A 3/1974 Takahashi et al.
3,813,687 A 5/1974 Geil
(Continued)

FOREIGN PATENT DOCUMENTS

AU 2005274099 10/2010
AU 20070325096 4/2012
(Continued)

OTHER PUBLICATIONS

NovaSound Int., http://www.novasoundint.com/new_page_t.htm, 2004.

*Primary Examiner* — Lun-See Lao
(74) *Attorney, Agent, or Firm* — Malloy & Malloy, P.L.

(57) ABSTRACT

The present invention provides for systems and methods for acquiring acoustic information from a resonating body. Specifically, a focused light beam is emitted from an emitter module onto an impedance matching reflector. The impedance matching reflector has similar wave propagation characteristics to the resonating body, so as to capture mechanical vibrations thereof. The impedance matching reflector reflects the focused light beam as it vibrates, and the vibrations are captured by a receiver module through the reflected light beam, which is converted to an input signal. The input signal may be further processed and converted to an audio output signal, as an accurate representation of the acoustic information emanating from within the resonating body.

18 Claims, 4 Drawing Sheets

(51) Int. Cl.
  *H04R 23/00* (2006.01)
  *G01N 29/14* (2006.01)
  *G01H 9/00* (2006.01)

(58) Field of Classification Search
  CPC .. H04M 3/53366; H04M 9/085; H04M 1/035;
      H04M 1/05; H04M 1/17; H04M 1/19;
      H04M 1/605; H04M 3/568; H04M
      1/0202
  USPC ..... 381/67, 172, 356, 357, 91, 122, 313, 92;
      356/900, 496–499; 385/12
  See application file for complete search history.

(56) References Cited

U.S. PATENT DOCUMENTS

| | | |
|---|---|---|
| 4,162,462 A | 7/1979 | Endoh et al. |
| 4,184,047 A | 1/1980 | Langford |
| 4,218,950 A | 8/1980 | Uetrecht |
| 4,226,533 A * | 10/1980 | Snowman ............ G08B 17/107 250/574 |
| 4,257,325 A | 3/1981 | Bertagni |
| 4,353,035 A | 10/1982 | Schröder |
| 4,356,558 A | 10/1982 | Owen et al. |
| 4,363,007 A | 12/1982 | Haramoto et al. |
| 4,412,100 A | 10/1983 | Orban |
| 4,517,415 A | 5/1985 | Laurence |
| 4,538,297 A | 8/1985 | Waller |
| 4,549,289 A | 10/1985 | Schwartz et al. |
| 4,584,700 A | 4/1986 | Scholz |
| 4,602,381 A | 7/1986 | Cugnini et al. |
| 4,612,665 A | 9/1986 | Inami et al. |
| 4,641,361 A | 2/1987 | Rosback |
| 4,677,645 A | 6/1987 | Kaniwa et al. |
| 4,696,044 A | 9/1987 | Waller, Jr. |
| 4,701,953 A | 10/1987 | White |
| 4,704,726 A | 11/1987 | Gibson |
| 4,715,559 A | 12/1987 | Fuller |
| 4,739,514 A | 4/1988 | Short et al. |
| 4,815,142 A | 3/1989 | Imreh |
| 4,856,068 A | 8/1989 | Quatieri, Jr. et al. |
| 4,887,299 A | 12/1989 | Cummins et al. |
| 4,997,058 A | 3/1991 | Bertagni |
| 5,007,707 A | 4/1991 | Bertagni |
| 5,073,936 A | 12/1991 | Gurike et al. |
| 5,133,015 A | 7/1992 | Scholz |
| 5,210,806 A | 5/1993 | Kihara et al. |
| 5,239,997 A | 8/1993 | Guarino et al. |
| 5,355,417 A | 10/1994 | Burdisso et al. |
| 5,361,381 A | 11/1994 | Short |
| 5,420,929 A | 5/1995 | Geddes et al. |
| 5,425,107 A | 6/1995 | Bertagni et al. |
| 5,463,695 A | 10/1995 | Werrbach |
| 5,465,421 A | 11/1995 | McCormick et al. |
| 5,467,775 A | 11/1995 | Callahan et al. |
| 5,473,214 A | 12/1995 | Hildebrand |
| 5,515,444 A | 5/1996 | Burdisso et al. |
| 5,539,835 A | 7/1996 | Bertagni et al. |
| 5,541,866 A | 7/1996 | Sato et al. |
| 5,572,443 A | 11/1996 | Emoto et al. |
| 5,615,275 A | 3/1997 | Bertagni |
| 5,617,480 A | 4/1997 | Ballard et al. |
| 5,638,456 A | 6/1997 | Conley et al. |
| 5,640,685 A | 6/1997 | Komoda |
| 5,671,287 A | 9/1997 | Gerzon |
| 5,693,917 A | 12/1997 | Bertagni et al. |
| 5,699,438 A | 12/1997 | Smith et al. |
| 5,727,074 A | 3/1998 | Hildebrand |
| 5,737,432 A | 4/1998 | Werrbach |
| 5,828,768 A | 10/1998 | Eatwell et al. |
| 5,832,097 A | 11/1998 | Armstrong et al. |
| 5,838,805 A | 11/1998 | Warnaka et al. |
| 5,848,164 A | 12/1998 | Levine |
| 5,872,852 A | 2/1999 | Dougherty |
| 5,901,231 A | 5/1999 | Parrella et al. |
| 5,990,955 A | 11/1999 | Koz |
| 6,058,196 A | 5/2000 | Heron |
| 6,078,670 A | 6/2000 | Beyer |
| 6,093,144 A | 7/2000 | Jaeger et al. |
| 6,108,431 A | 8/2000 | Bachler |
| 6,201,873 B1 | 3/2001 | Dal Farra |
| 6,202,601 B1 | 3/2001 | Ouellette et al. |
| 6,208,237 B1 | 3/2001 | Saiki et al. |
| 6,263,354 B1 | 7/2001 | Gandhi |
| 6,285,767 B1 | 9/2001 | Klayman |
| 6,292,511 B1 | 9/2001 | Goldston et al. |
| 6,317,117 B1 | 11/2001 | Goff |
| 6,318,797 B1 | 11/2001 | Böhm et al. |
| 6,332,029 B1 | 12/2001 | Azima et al. |
| 6,518,852 B1 | 2/2003 | Derrick |
| 6,535,846 B1 | 3/2003 | Shashoua |
| 6,570,993 B1 | 5/2003 | Fukuyama |
| 6,618,487 B1 | 9/2003 | Azima et al. |
| 6,661,897 B2 | 12/2003 | Smith |
| 6,661,900 B1 | 12/2003 | Allred et al. |
| 6,772,114 B1 | 8/2004 | Sluijter et al. |
| 6,847,258 B2 | 1/2005 | Ishida et al. |
| 6,871,525 B2 | 3/2005 | Withnall et al. |
| 6,907,391 B2 | 6/2005 | Bellora et al. |
| 6,999,826 B1 | 2/2006 | Zhou et al. |
| 7,006,653 B2 | 2/2006 | Guenther |
| 7,016,746 B2 | 3/2006 | Wiser et al. |
| 7,024,001 B1 | 4/2006 | Nakada |
| 7,058,463 B1 | 6/2006 | Ruha et al. |
| 7,123,728 B2 | 10/2006 | King et al. |
| 7,254,243 B2 | 8/2007 | Bongiovi |
| 7,266,205 B2 | 9/2007 | Miller |
| 7,274,795 B2 | 9/2007 | Bongiovi |
| 7,519,189 B2 | 4/2009 | Bongiovi |
| 7,577,263 B2 | 8/2009 | Tourwe |
| 7,613,314 B2 | 11/2009 | Camp, Jr. |
| 7,676,048 B2 | 3/2010 | Tsutsui |
| 7,711,442 B2 | 5/2010 | Ryle et al. |
| 7,778,718 B2 | 8/2010 | Janke et al. |
| 7,916,876 B1 | 3/2011 | Helsloot |
| 8,068,621 B2 | 11/2011 | Okabayashi et al. |
| 8,160,274 B2 | 4/2012 | Bongiovi |
| 8,175,287 B2 | 5/2012 | Ueno et al. |
| 8,229,136 B2 | 7/2012 | Bongiovi |
| 8,284,955 B2 | 10/2012 | Bongiovi et al. |
| 8,462,963 B2 | 6/2013 | Bongiovi |
| 8,472,642 B2 | 6/2013 | Bongiovi |
| 8,503,701 B2 * | 8/2013 | Miles ................... H04R 23/006 356/498 |
| 8,565,449 B2 | 10/2013 | Bongiovi |
| 8,705,765 B2 | 4/2014 | Bongiovi |
| 8,879,743 B1 | 11/2014 | Mitra |
| 9,195,433 B2 | 11/2015 | Bongiovi et al. |
| 9,264,004 B2 | 2/2016 | Bongiovi et al. |
| 9,276,542 B2 | 3/2016 | Bongiovi et al. |
| 9,281,794 B1 | 3/2016 | Bongiovi et al. |
| 9,344,828 B2 | 5/2016 | Bongiovi et al. |
| 9,348,904 B2 | 5/2016 | Bongiovi et al. |
| 9,350,309 B2 | 5/2016 | Bongiovi et al. |
| 9,397,629 B2 | 7/2016 | Bongiovi et al. |
| 9,398,394 B2 | 7/2016 | Bongiovi et al. |
| 2001/0008535 A1 | 7/2001 | Lanigan |
| 2001/0043704 A1 | 11/2001 | Schwartz |
| 2002/0057808 A1 | 5/2002 | Goldstein |
| 2002/0094096 A1 * | 7/2002 | Paritsky ............... H04R 23/008 381/172 |
| 2003/0016838 A1 * | 1/2003 | Paritsky ............... H04R 23/008 381/172 |
| 2003/0023429 A1 | 1/2003 | Claesson |
| 2003/0035555 A1 | 2/2003 | King et al. |
| 2003/0043940 A1 | 3/2003 | Janky et al. |
| 2003/0112088 A1 | 6/2003 | Bizjak |
| 2003/0138117 A1 | 7/2003 | Goff |
| 2003/0142841 A1 | 7/2003 | Wiegand |
| 2003/0164546 A1 | 9/2003 | Giger |
| 2003/0179891 A1 | 9/2003 | Rabinowitz et al. |
| 2003/0216907 A1 | 11/2003 | Thomas |
| 2004/0003805 A1 | 1/2004 | Ono et al. |
| 2004/0022400 A1 | 2/2004 | Magrath |

(56) References Cited

U.S. PATENT DOCUMENTS

| | | |
|---|---|---|
| 2004/0044804 A1 | 3/2004 | MacFarlane |
| 2004/0086144 A1 | 5/2004 | Kallen |
| 2004/0138769 A1 | 7/2004 | Akiho |
| 2004/0146170 A1 | 7/2004 | Zint |
| 2005/0090295 A1 | 4/2005 | Ali et al. |
| 2005/0117771 A1 | 6/2005 | Vosburgh et al. |
| 2005/0129248 A1 | 6/2005 | Kraemer et al. |
| 2005/0175185 A1 | 8/2005 | Korner |
| 2005/0201572 A1 | 9/2005 | Lindahl et al. |
| 2005/0249272 A1 | 11/2005 | Kirkeby et al. |
| 2005/0254564 A1 | 11/2005 | Tsutsui |
| 2006/0034467 A1 | 2/2006 | Sleboda et al. |
| 2006/0064301 A1 | 3/2006 | Aguilar et al. |
| 2006/0098827 A1 | 5/2006 | Paddock et al. |
| 2006/0126851 A1 | 6/2006 | Yuen et al. |
| 2006/0126865 A1 | 6/2006 | Blamey et al. |
| 2006/0138285 A1 | 6/2006 | Oleski et al. |
| 2006/0140319 A1 | 6/2006 | Eldredge et al. |
| 2006/0189841 A1 | 8/2006 | Pluvinage |
| 2006/0291670 A1 | 12/2006 | King et al. |
| 2007/0010132 A1 | 1/2007 | Nelson |
| 2007/0119421 A1 | 5/2007 | Lewis et al. |
| 2007/0173990 A1 | 7/2007 | Smith et al. |
| 2007/0177459 A1 | 8/2007 | Behn |
| 2007/0206643 A1 | 9/2007 | Egan |
| 2007/0223713 A1 | 9/2007 | Gunness |
| 2007/0223717 A1 | 9/2007 | Boersma |
| 2007/0253577 A1 | 11/2007 | Yen et al. |
| 2008/0031462 A1 | 2/2008 | Walsh et al. |
| 2008/0040116 A1 | 2/2008 | Cronin |
| 2008/0069385 A1 | 3/2008 | Revit |
| 2008/0112576 A1 | 5/2008 | Bongiovi |
| 2008/0123870 A1 | 5/2008 | Stark |
| 2008/0123873 A1 | 5/2008 | Bjorn-Josefsen et al. |
| 2008/0137881 A1 | 6/2008 | Bongiovi |
| 2008/0165989 A1 | 7/2008 | Seil et al. |
| 2008/0181424 A1 | 7/2008 | Schulein et al. |
| 2008/0219459 A1 | 9/2008 | Bongiovi et al. |
| 2008/0255855 A1 | 10/2008 | Lee et al. |
| 2009/0022328 A1 | 1/2009 | Neugebauer et al. |
| 2009/0054109 A1 | 2/2009 | Hunt |
| 2009/0062946 A1 | 3/2009 | Bongiovi et al. |
| 2009/0086996 A1 | 4/2009 | Bongiovi et al. |
| 2009/0282810 A1 | 11/2009 | Leone et al. |
| 2009/0290725 A1 | 11/2009 | Huang |
| 2009/0296959 A1 | 12/2009 | Bongiovi |
| 2010/0166222 A1 | 7/2010 | Bongiovi |
| 2010/0256843 A1 | 10/2010 | Bergstein et al. |
| 2010/0278364 A1 | 11/2010 | Berg |
| 2010/0303278 A1 | 12/2010 | Sahyoun |
| 2011/0013736 A1 | 1/2011 | Tsukamoto et al. |
| 2011/0087346 A1 | 4/2011 | Larsen et al. |
| 2011/0194712 A1 | 8/2011 | Potard |
| 2011/0230137 A1 | 9/2011 | Hicks et al. |
| 2011/0257833 A1 | 10/2011 | Trush et al. |
| 2012/0014553 A1 | 1/2012 | Bonanno |
| 2012/0099741 A1 | 4/2012 | Gotoh et al. |
| 2012/0170759 A1 | 7/2012 | Yuen et al. |
| 2012/0213034 A1 | 8/2012 | Imran |
| 2012/0213375 A1 | 8/2012 | Mahabub et al. |
| 2012/0302920 A1 | 11/2012 | Bridger et al. |
| 2013/0121507 A1 | 5/2013 | Bongiovi et al. |
| 2013/0162908 A1 | 6/2013 | Son et al. |
| 2013/0163783 A1 | 6/2013 | Burlingame |
| 2013/0169779 A1 | 7/2013 | Pedersen |
| 2013/0220274 A1 | 8/2013 | Deshpande et al. |
| 2013/0227631 A1 | 8/2013 | Sharma et al. |
| 2013/0242191 A1 | 9/2013 | Leyendecker |
| 2013/0288596 A1 | 10/2013 | Suzuki et al. |
| 2013/0338504 A1 | 12/2013 | Demos et al. |
| 2014/0067236 A1 | 3/2014 | Henry et al. |
| 2014/0100682 A1 | 4/2014 | Bongiovi |
| 2014/0112497 A1 | 4/2014 | Bongiovi |
| 2014/0153765 A1 | 6/2014 | Gan et al. |
| 2014/0185829 A1 | 7/2014 | Bongiovi |
| 2014/0261301 A1 | 9/2014 | Leone |
| 2014/0369504 A1 | 12/2014 | Bongiovi |
| 2014/0379355 A1 | 12/2014 | Hosokawsa |
| 2015/0215720 A1 | 7/2015 | Carroll |
| 2015/0297169 A1 | 10/2015 | Copt et al. |
| 2015/0297170 A1 | 10/2015 | Copt et al. |
| 2016/0036402 A1 | 2/2016 | Bongiovi et al. |
| 2016/0044436 A1 | 2/2016 | Copt et al. |
| 2016/0240208 A1 | 8/2016 | Bongiovi et al. |
| 2016/0258907 A1 | 9/2016 | Butera, III et al. |
| 2016/0344361 A1 | 11/2016 | Bongiovi et al. |
| 2017/0033755 A1 | 2/2017 | Bongiovi et al. |
| 2017/0041732 A1 | 2/2017 | Bongiovi et al. |

FOREIGN PATENT DOCUMENTS

| | | |
|---|---|---|
| AU | 2012202127 | 7/2014 |
| BR | 96114177 | 2/1999 |
| BR | 96113723 | 7/1999 |
| CA | 2533221 | 6/1995 |
| CA | 2161412 | 4/2000 |
| CA | 2576829 | 7/2014 |
| CN | 1173268 | 2/1998 |
| CN | 12221528 | 6/1999 |
| CN | 101536541 | 9/2009 |
| CN | 101946526 | 1/2011 |
| CN | 102265641 | 11/2011 |
| CN | 102652337 | 8/2012 |
| CN | 103004237 | 3/2013 |
| CN | 0780050323 | 5/2013 |
| CN | 203057339 | 7/2013 |
| EP | 0206746 B1 | 8/1992 |
| EP | 0541646 | 1/1995 |
| EP | 0580579 | 6/1998 |
| EP | 0698298 | 2/2000 |
| EP | 0932523 | 6/2000 |
| EP | 0666012 | 11/2002 |
| EP | 2814267 B1 | 10/2016 |
| ES | 2218599 | 10/1998 |
| ES | 2249788 | 10/1998 |
| ES | 2219949 | 8/1999 |
| GB | 2003707 A | 3/1979 |
| GB | 2320393 | 12/1996 |
| ID | P0031074 | 6/2012 |
| IN | 260362 | 4/2014 |
| IS | 198914 | 7/2014 |
| JP | 3150910 | 6/1991 |
| JP | 7106876 | 4/1995 |
| JP | 1020040022442 | 3/2004 |
| JP | 2005500768 | 1/2005 |
| JP | 1020090101209 | 9/2009 |
| JP | 4787255 | 7/2011 |
| JP | 5048782 | 7/2012 |
| JP | 201543561 | 3/2015 |
| KR | 1020040022442 | 3/2004 |
| KR | 1020090101209 | 9/2009 |
| KR | 101503541 | 3/2015 |
| MO | J001182 | 10/2013 |
| MX | 274143 | 8/2005 |
| MX | 301172 | 11/2006 |
| MX | 315197 | 11/2013 |
| NZ | 553744 | 1/2009 |
| NZ | 574141 | 4/2010 |
| NZ | 557201 | 5/2012 |
| PH | 12009501073 | 11/2014 |
| RU | 2407142 | 12/2010 |
| RU | 2483363 | 5/2013 |
| SG | 152762 | 12/2011 |
| SG | 155213 | 2/2013 |
| SU | 1319288 | 6/1987 |
| WO | WO 9219080 | 10/1992 |
| WO | WO 9311637 | 6/1993 |
| WO | WO 9321743 | 10/1993 |
| WO | WO 9427331 | 11/1994 |
| WO | WO 9514296 | 5/1995 |
| WO | WO 9531805 | 11/1995 |
| WO | WO 9535628 | 12/1995 |
| WO | WO 9601547 | 1/1996 |
| WO | WO 9611465 | 4/1996 |

(56) References Cited

FOREIGN PATENT DOCUMENTS

| | | |
|---|---|---|
| WO | WO 9708847 | 3/1997 |
| WO | WO 9709698 | 3/1997 |
| WO | WO 9709840 | 3/1997 |
| WO | WO 9709841 | 3/1997 |
| WO | WO 9709842 | 3/1997 |
| WO | WO 9709843 | 3/1997 |
| WO | WO 9709844 | 3/1997 |
| WO | WO 9709845 | 3/1997 |
| WO | WO 9709846 | 3/1997 |
| WO | WO 9709848 | 3/1997 |
| WO | WO 9709849 | 3/1997 |
| WO | WO 9709852 | 3/1997 |
| WO | WO 9709853 | 3/1997 |
| WO | WO 9709854 | 3/1997 |
| WO | WO 9709855 | 3/1997 |
| WO | WO 9709856 | 3/1997 |
| WO | WO 9709857 | 3/1997 |
| WO | WO 9709858 | 3/1997 |
| WO | WO 9709859 | 3/1997 |
| WO | WO 9709861 | 3/1997 |
| WO | WO 9709862 | 3/1997 |
| WO | WO 9717818 | 5/1997 |
| WO | WO 9717820 | 5/1997 |
| WO | WO 9813942 | 4/1998 |
| WO | WO 9816409 | 4/1998 |
| WO | WO 9828942 | 7/1998 |
| WO | WO 9831188 | 7/1998 |
| WO | WO 9834320 | 8/1998 |
| WO | WO 9839947 | 9/1998 |
| WO | WO 9842536 | 10/1998 |
| WO | WO 9843464 | 10/1998 |
| WO | WO 9852381 | 11/1998 |
| WO | WO 9852383 | 11/1998 |
| WO | WO 9853638 | 11/1998 |
| WO | WO 9902012 | 1/1999 |
| WO | WO 9908479 | 2/1999 |
| WO | WO 9911490 | 3/1999 |
| WO | WO 9912387 | 3/1999 |
| WO | WO 9913684 | 3/1999 |
| WO | WO 9921397 | 4/1999 |
| WO | WO 9935636 | 7/1999 |
| WO | WO 9935883 | 7/1999 |
| WO | WO 9937121 | 7/1999 |
| WO | WO 9938155 | 7/1999 |
| WO | WO 9941939 | 8/1999 |
| WO | WO 9952322 | 10/1999 |
| WO | WO 9952324 | 10/1999 |
| WO | WO 9956497 | 11/1999 |
| WO | WO 9962294 | 12/1999 |
| WO | WO 9965274 | 12/1999 |
| WO | WO 0001264 | 1/2000 |
| WO | WO 0002417 | 1/2000 |
| WO | WO 0007408 | 2/2000 |
| WO | WO 0007409 | 2/2000 |
| WO | WO 0013464 | 3/2000 |
| WO | WO 0015003 | 3/2000 |
| WO | WO 0033612 | 6/2000 |
| WO | WO 0033613 | 6/2000 |
| WO | WO 03104924 | 12/2003 |
| WO | WO 2006020427 | 2/2006 |
| WO | WO 2007092420 | 8/2007 |
| WO | WO 2008067454 | 6/2008 |
| WO | WO 2009070797 | 6/2009 |
| WO | WO 2009114746 | 9/2009 |
| WO | WO 2009155057 | 12/2009 |
| WO | WO 2010027705 | 3/2010 |
| WO | WO 2010051354 | 5/2010 |
| WO | WO 2011081965 | 7/2011 |
| WO | WO 2013055394 | 4/2013 |
| WO | WO 2013076223 | 5/2013 |
| WO | WO2014201103 A1 | 12/2014 |
| WO | WO 2015061393 | 4/2015 |
| WO | WO 2015077681 | 5/2015 |
| WO | WO 2015161034 | 10/2015 |
| WO | WO 2016019263 | 2/2016 |
| WO | WO 2016022422 | 2/2016 |
| WO | WO2016144861 | 9/2016 |

\* cited by examiner

SYSTEM AND METHOD FOR ACQUIRING ACOUSTIC INFORMATION FROM A RESONATING BODY

FIELD OF THE INVENTION

The present invention provides for a system and method for acquiring acoustic information from a resonating body. Specifically, a light beam is used to measure the vibration of a reflective surface attached to an acoustic analog having similar mechanical properties as those of the resonating body, in order to acquire accurate acoustic information from within the resonating body.

BACKGROUND OF THE INVENTION

Auscultation relates to the listening of internal sounds within the body, and is performed for purposes of examining the circulatory system, respiratory system, as well as gastrointestinal system within a human or animal body. Auscultation may also be performed on a mechanical body, such as listening to the engine of a vehicle.

Auscultation is typically performed by using a stethoscope, which captures sound from a body through a diaphragm or bell. When the diaphragm or bell is placed directly against the body, it receives sound vibrations from therein, that then create acoustic pressure waves which travel up the tubing to a listener's ears.

One problem with traditional acoustic stethoscopes however, is the low sound volume and quality, due to a loss of signal when vibrations are transmitted between materials of different mechanical properties, i.e. the resonating human or animal body and the diaphragm or bell of the stethoscope. These different mechanical properties, such as density, impedance, vibration transmission speed, etc., affect the sound signal differently as it travels from the body to the stethoscope.

Another problem arises in high noise environments, for example, such as auscultation by a medical personnel in an ambulance or helicopter. In these types of situations, external noise will interfere with the diaphragm or bell of a stethoscope, which may either drown out or otherwise affect the auscultation sounds.

Therefore, there is a need in the art to accurately capture or acquire acoustic information from within a resonating body, while minimizing the loss of signal from transference between the body and the stethoscope, as well as noise interference from the external environment.

SUMMARY OF THE INVENTION

The present invention meets the existing needs described above by providing for systems and methods for acquiring accurate acoustic information from a resonating body, regardless of the external environment.

Accordingly, in initially broad terms, a laser or other focused light source is used to measure the vibrations of a reflective surface embedded in or attached to an optically transparent material with similar mechanical properties to a resonating body that contains the acoustic signal. This matching of the mechanical properties, and subsequent vibroscopy within the impedance matched system allows for the collection of an accurate sound signal.

As such, a system of the present invention comprises an emitter module, an impedance matching reflector, a receiver module, and may also comprise a housing. At least one system of the present invention may be directed to a medical stethoscope for listening to internal sounds of a human or animal body.

Emitter module is structured and configured to emit a focused light beam, such as a laser, onto the impedance matching reflector in order to create a reflected light beam.

The impedance matching reflector is structured to have wave propagation characteristics similar to the resonating body, so that it may vibrate at a similar frequency and share similar sound impedance and other acoustic transference characteristics as the resonating body. Impedance matching reflector may comprise an impedance matching lens and a reflective surface embedded or affixed therein. The impedance matching lens preferably comprises an optically transparent material, such as an acrylic lens or a ballistics gel. The reflective surface may comprise a mirror formed of appropriate materials so as to reflect the emitted focused light beam onto the receiver module.

The receiver module is structured to detect the light intensity of the reflected light beam and/or vibrations or other characteristics thereof, in order to create an input signal. The input signal may be modified by an audio processor for sound enhancement and/or noise reduction. The input signal is converted to an output audio signal through an audio transducer forming part of, or in communication with, the receiver module.

In other embodiments of the present invention directed to methods for acquiring acoustic information from a resonating body, an impedance matching reflector may first be positioned in vibrational transference relations to a resonating body. A focused light beam is then emitted from an emitter module onto the impedance matching reflector in order to create a reflected light beam. The reflected light beam is then received at a receiver module as the impedance matching reflector vibrates in accordance with the resonating body. The reflected light beam is further converted by the receiver module in order to create an input signal. The input signal may further be processed and/or converted into an audio output signal with an audio transducer.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE EMBODIMENT

As illustrated by the accompanying drawings, the present invention is directed to a system and method for acquiring acoustic information from a resonating body. Specifically, some embodiments of the present invention relate to the use of a focused light beam in order to measure the vibrations of an impedance matching reflector in vibrational transference relations to a resonating body.

Figure 1:
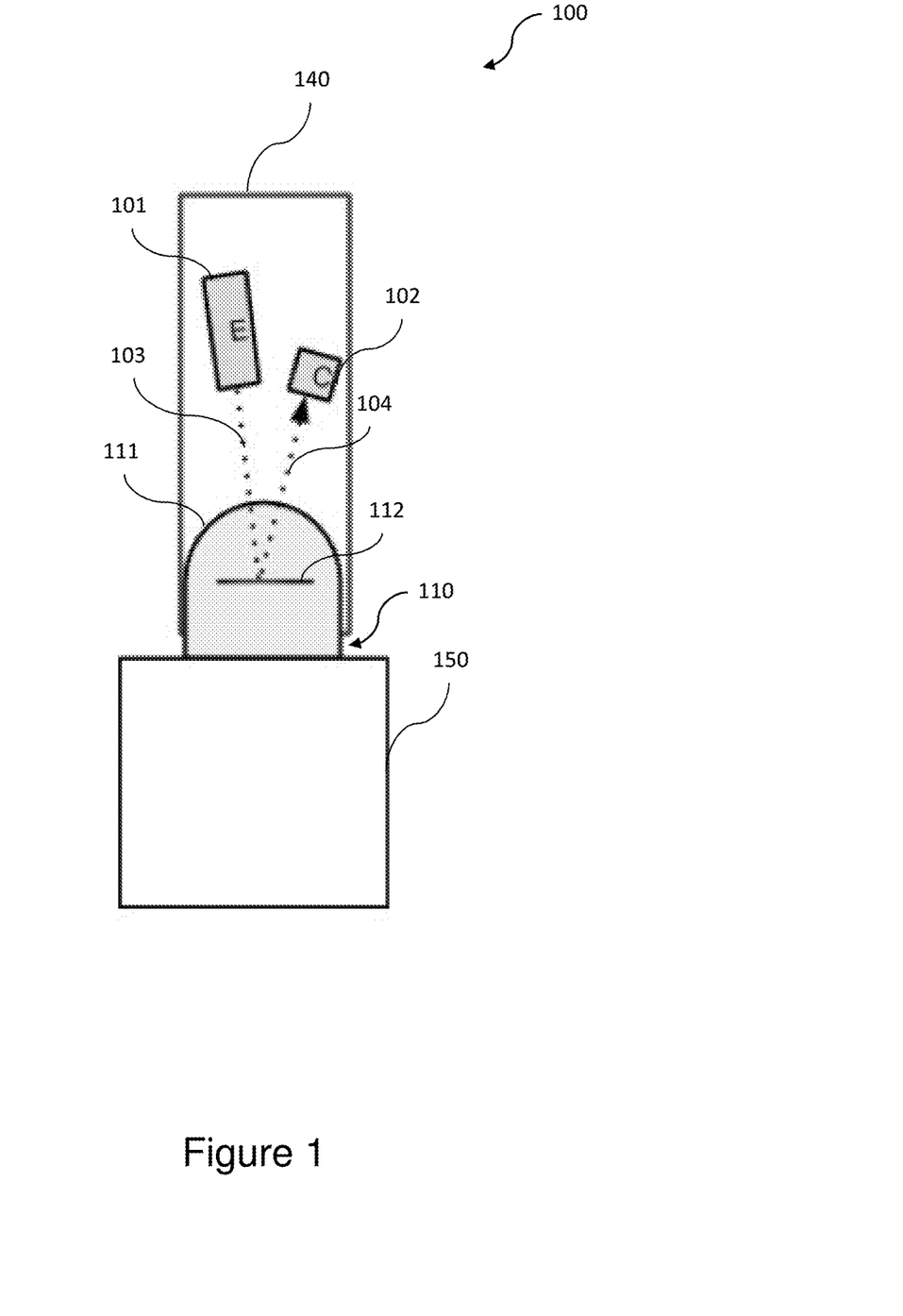
FIG. 1 is a schematic representation of a system for acquiring acoustic information from a resonating body.

Accordingly, as schematically represented in FIG. 1, one embodiment of the present invention may comprise a system 100 for acquiring acoustic information from a resonating body 150. System 100 may comprise an emitter module 101, an impedance matching reflector 110, a receiver module 102, and may further comprise a housing 140 structured to stabilize the internal components. Resonating body 150 may comprise any object or body capable of emitting sound from within. In at least one embodiment of the present invention, the system 100 is used as a stethoscope to acquire acoustic information from a human or animal body.

Emitter module 101 is structured and configured to emit a focused light beam onto the impedance matching reflector 110 in order to create a reflected light beam. In a preferred embodiment, the emitter module 101 will be structured to create a highly collimated light beam such as a laser. Accordingly, emitter module 101 may comprise at least one laser diode. The laser diode may comprise a double heterostructure laser diode, quantum well laser diode, distributed Bragg reflector laser diode, distributed feedback laser diode, vertical-cavity surface-emitting laser (VCSEL) diode, vertical-external-cavity surface-emitting-laser diode (VECSEL) diode, and other laser diodes known to those skilled in the art. In other embodiments, the emitter module 101 may be structured to create other appropriately focused light beams which may also be measurable in intensity and/or movement.

Impedance matching reflector 110 is structured to have wave propagation characteristic substantially similar to the resonating body, so as to vibrate at a substantially similar frequency as the resonating body. For instance, the impedance matching reflector 110 may comprise a similar density or have similar acoustic impedance as the resonating body. At least a portion of the impedance matching reflector 110 is placed in vibrational transference relations to the resonating body, so as to receive mechanical vibrations and vibrate in a similar fashion or at a similar frequency as the resonating body.

In a preferred embodiment of the present invention, the impedance matching reflector 110 may comprise an impedance matching lens 111 and a reflective surface 112 embedded therein. The impedance matching lens 111 comprises an optically transparent material. In at least one embodiment where it may be desirable to measure a solid structure, the impedance matching lens 111 may comprise an acrylic lens. The acrylic lens may comprise polymethyl methacrylate or other appropriate and transparent acrylic polymers. In at least one embodiment of the present invention comprising housing 140 structured to enclose the emitter module 101, receiver module 102, and impedance matching reflector 110, at least a portion of the impedance matching reflector 110 may be exposed externally to the housing 140, such as to make direct physical contact with the resonating body 150. This exposed area of the impedance matching reflector 110 is the equivalent of the "diaphragm" and/or "bell" of a traditional stethoscope.

Figure 2:
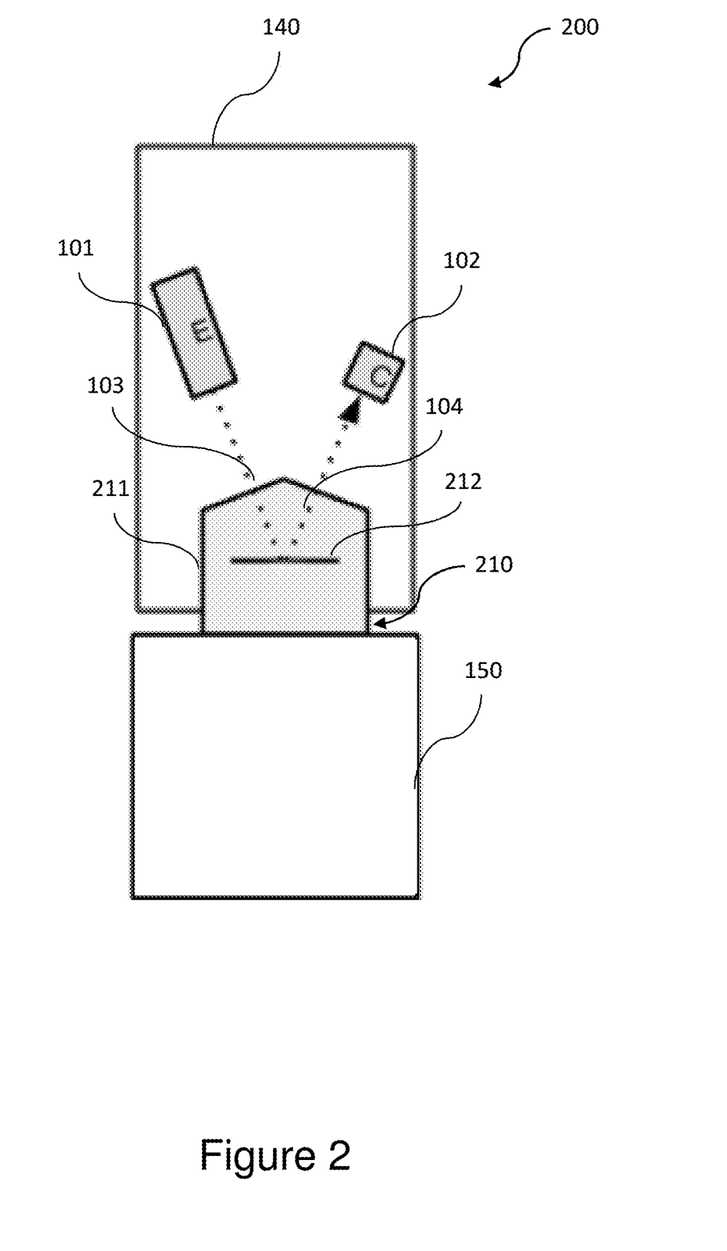
FIG. 2 is a schematic representation of a system for acquiring acoustic information from a resonating body comprising a different impedance matching reflector configuration.

In at least one embodiment of the present invention directed to medical stethoscopes, the impedance matching lens 111 may comprise a ballistics gelatin or gel that simulates the density and viscosity of human or animal tissue. The ballistics gel preferably comprises a synthetic gel that may be reusable and may be reformed without affecting the properties of the gel. Different ballistics gels having various densities and viscosities may be formulated for different tissues, in order to provide for a closer simulation of the vibrational characteristics of the resonating body, which may in this embodiment comprise muscle tissue, epithelial tissue, connective tissue, and nervous tissue. In some embodiments of the present invention, a combination of optically clear acrylic and clear ballistics gel may be used to form the impedance matching lens 111. The impedance matching lens 111, 211, and 311 may comprise different profiles, such as a semi-dome or semi-spherical profile as shown in system 100 of FIG. 1, a prismatic profile as shown in system 200 of FIG. 3, a cuboid profile as shown in system 300 of FIG. 3, or other shapes or profiles depending on the positioning of the emitter module 101 and receiver module 102 and desired reflection angle of the light beam 103.

Figure 3:
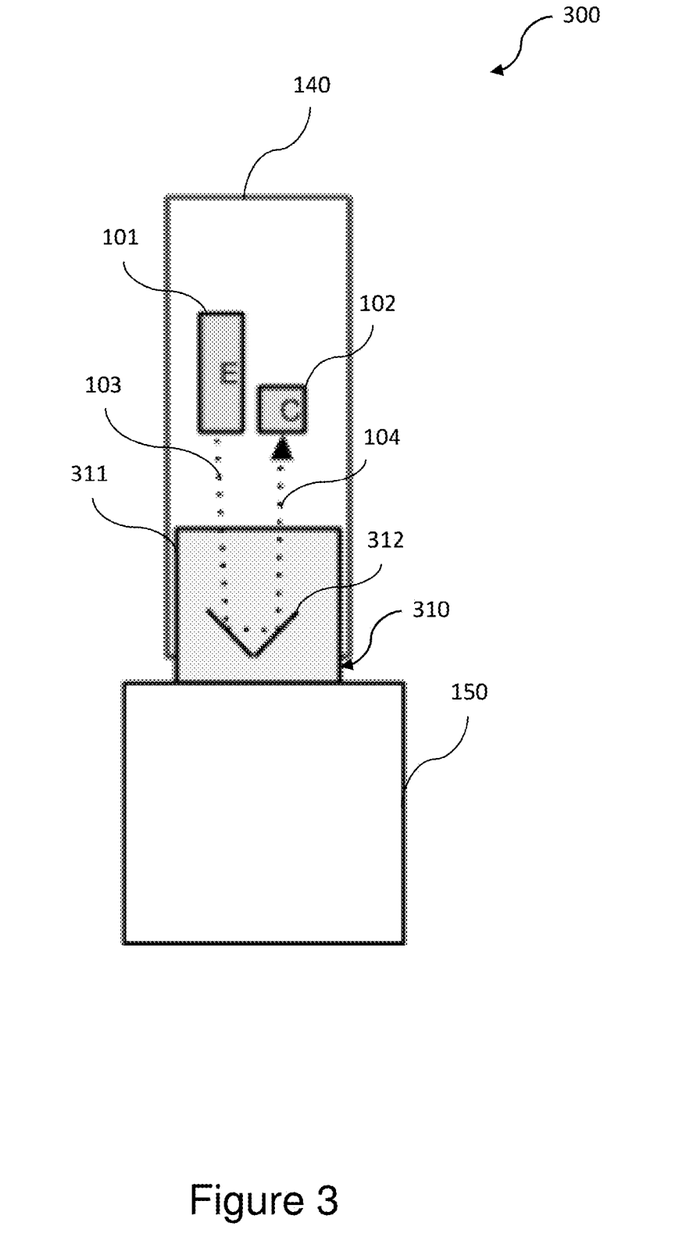
FIG. 3 is a schematic representation of a system for acquiring acoustic information from a resonating body comprising another impedance matching reflector configuration.

The reflective surface 112 is configured to reflect the focused light beam 103 created by the emitter module 101 to the receiver module 102 as a reflected light beam 104. Accordingly, reflective surface 112 may be embedded, suspended, or otherwise affixed within the impedance matching lens 111. Reflective surface 112 may comprise a mirror or other suitable materials having a reflective coating on an appropriate substrate. In a preferred embodiment, it may be desirable to use a thin and lightweight material so as to not affect the wave propagation characteristics of the impedance matching lens 111. The reflective surface 112 may further be optimized for desired use by altering its reflective properties. The reflective surface 112, 212 may comprise a substantially flat surface as illustrated in system 100 of FIG. 1 or system 200 of FIG. 2. The reflective surface 312 may also comprise a surface having two reflective segments connected at a right angle, so as to reflect the light beam 103 created by the emitter module 101 as reflected light beam 104 to receiver module 102 when the two modules are placed in closer proximity to each other. Of course, other number of reflective segments, flat and/or curved profiles, various shapes of the reflect surfaces or segments may be used, depending on the desired positioning of the emitter module 101 and receiver module 102, as well as the desired light reflective and refractive characteristics.

Receiver module 102 is structured to detect the light intensity and/or vibrations in the reflected light beam 104 as it vibrates in accordance with the impedance matching reflector 310. The receiver module 102 is further configured to convert the reflected light beam into an input signal. Accordingly, receiver module 102 may comprise a light transducer that includes at least one photodetector or light sensor. The photodetector may comprise at least one photo diode, photo resistor, optical detector, photoresistor, photovoltaic cell, photomultiplier, phototube, phototransistor, charge coupled device (CCD).

Receiver module 102 may further comprise an audio processor for modifying the input signal. The processing module may comprise a digital signal processor, amplifier, filters, and volume controls. Processing module may comprise processor and combination of circuits structured to further enhance the audio quality of the signal coming from the microphone preamplifier, such as but not limited to shelf filters, equalizers, modulators. For example, in at least one embodiment the audio processor may comprise a processor that performs the steps for processing a signal as taught by the present inventor's U.S. Pat. No. 8,160,274. Audio processor may incorporate various acoustic profiles customized for a user and/or for an environment, such as those described in the present inventor's U.S. Pat. No. 8,565,449. Audio processor may additionally incorporate processing suitable for high noise environments, such as those described in the present inventor's U.S. Pat. No. 8,462,963. Parameters of the audio processor may be controlled and modified by a user via any means known to one skilled in the art, such as by a direct interface or a wireless communication interface.

The housing 140 is structured to substantially enclose the components of the present invention, including the emitter module 101, receiver module 102, impedance matching reflector 110 and the impedance matching lens 111 and reflective surface 112 thereof. Housing 140 is ideally structured to stabilize the internal components therein, so as to provide for a consistent and accurate measurement regardless of external environment vibrations. Housing 140 is also ideally formed from an opaque material, such as to block out potential light interference that may comprise the reflected light beam emitted by the emitting module 101.

The present invention may further comprise an acoustic transducer, not shown, in communicable relations to the receiver module 102 and/or the audio processor thereof. The acoustic transducer is structured to convert the input signal from the receiver module 102 as audio signal. In at least one embodiment of the present invention, the acoustic transducer may be formed as part of a headset or speaker remotely connected to the receiver module 102 and/or the audio processor, such as via near-field communication or other wireless technologies. Of course, the acoustic transducer may also be connected via a wired connection to the receiver module 102 and/or the audio processor.

Figure 4:
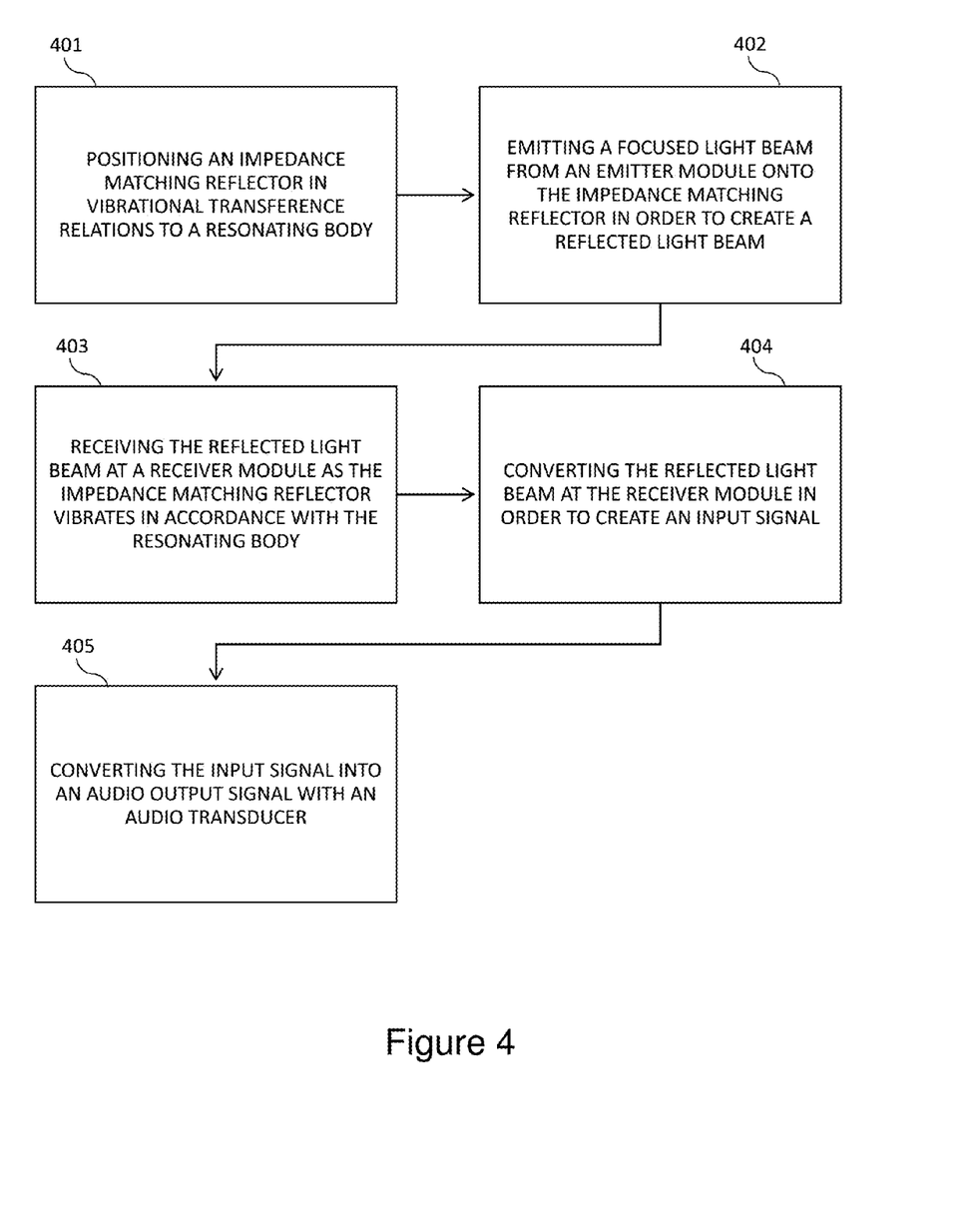
FIG. 4 is a flowchart directed to a method for acquiring acoustic information from a resonating body.

Drawing attention to FIG. 4, other embodiments of the present invention are drawn to methods for acquiring acoustic information from a resonating body. Accordingly, an impedance matching reflector is first positioned in vibrational transference relations to a resonating body, as in 401. The impedance matching reflector may be positioned or placed in direct confronting relations to the resonating body, such that a majority of an exposed surface of the impedance matching reflector is in direct physical contact with the resonating body. The impedance matching reflector will ideally vibrate at the same frequency such that sound waves from the resonating body is accurately transferred to the impedance matching reflector. The impedance matching reflector may comprise an impedance matching lens and reflective surface embedded therein as described above.

A focused light beam is then emitted from an emitter module, as in 402, onto the impedance matching reflector in order to create a reflected light beam. In a preferred embodiment, the focused light beam is reflected off a reflective surface embedded within an impedance matching lens, as described above, such that the vibrational characteristics of the resonating body and impedance matching reflector is captured through the reflected light beam, as the light beam vibrates and changes in reflection angle and intensity.

The reflected light beam is received, as in 403, at a receiver module as the impedance matching reflector vibrates in accordance with the resonating body. As discussed above, the reflected light beam is captured at the receiver module as it changes in reflection angle and intensity. The receiver module may comprise a light transducer and/or a photodetector in accordance to the system of the present invention.

The reflected light beam is converted by the receiver module, as in 404, in order to create an input signal. As such, the light transducer and/or photodetector of the receiver module or forming part of the receiver module are appropriately structured and configured to receive changes in the reflected light beam, and convert the same as an input signal or electrical signal.

The input signal may further be converted, as in 405, into an audio output signal with an audio transducer. As such, the input signal may be transmitted to an audio transducer forming part of the receiver module or communicably connected to the receiver module as described in the system embodiments described above. The transducer may comprise a headset, a loud speaker, or any surface capable of acoustic resonance. The input signal may be processed by at least one audio processor in order to enhance the input signal such as by amplifying the desirable signals and/or filtering out extraneous noise.

It should be understood that the above steps may be conducted exclusively or nonexclusively and in any order. Further, the physical devices recited in the methods may comprise any apparatus and/or systems described within this document or known to those skilled in the art.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A system for acquiring acoustic information from a resonating body comprising:
   an emitter module configured to emit a focused light beam onto a reflective surface in order to create a reflected light beam,
   said reflective surface at least partially disposed within an impedance matching lens,
   said impedance matching lens is structured to have at least one wave propagation characteristic that is substantially similar to the resonating body, so as to vibrate at a substantially similar frequency as the resonating body,
   said impedance matching lens further disposable in direct confronting relation to the resonating body,
   a receiver module structured to detect the vibrations in the reflected light beam as it vibrates in accordance to said impedance matching lens, said receiver module is further configured to convert the reflected light beam into an input signal.

2. The system as recited in claim 1 further comprising an acoustic transducer structured to convert the input signal into an audio signal.

3. The system as recited in claim 1 wherein said receiver module comprises a light transducer structured to convert the reflected light signal into the input signal.

4. The system as recited in claim 3 wherein said emitter module comprises at least one laser diode.

5. The system as recited in claim 3 wherein said receiver module comprises at least one photo diode.

6. The system as recited in claim 3 wherein said receiver module comprises at least one photo resistor.

7. The system as recited in claim 3 wherein said receiver module comprises at least one charge coupled device.

8. The system as recited in claim 1 wherein said impedance matching lens comprises a substantially similar vibration transmission speed as the resonating body.

9. The system as recited in claim 1 wherein said impedance matching lens comprises a substantially similar density as the resonating body.

10. The system as recited in claim 1 wherein said impedance matching lens comprises a substantially similar acoustic impedance as the resonating body.

11. The system as recited in claim 1 wherein said impedance matching lens comprises an optically transparent material.

12. The system as recited in claim 11 wherein said impedance matching lens comprises a synthetic ballistics gel.

13. The system as recited in claim 11 wherein said impedance matching lens comprises an acrylic lens.

14. A method for acquiring acoustic information from a resonating body comprising:
preselecting an impedance matching reflector to correspond with an impedance of the resonating body,
positioning the impedance matching reflector in vibrational transference relations to the resonating body,
emitting a focused light beam from an emitter module onto the impedance matching reflector in order to create a reflected light beam,
receiving the reflected light beam at a receiver module as the impedance matching reflector vibrates in accordance with the resonating body,
converting the reflected light beam at the receiver module in order to create an input signal,
converting the input signal into an audio output signal with an audio transducer.

15. The method as recited in claim 14 comprising positioning the impedance matching reflector in direct confronting relations to the resonating body.

16. The method as recited in claim 14 comprising emitting a focused light beam from an emitter module onto a reflective surface within an impedance matching lens that together form the impedance matching reflector.

17. The method as recited in claim 14 wherein the focused light beam comprises a laser and the reflected light beam comprises a reflected laser.

18. The method as recited in claim 14 wherein the impedance matching reflector comprises at least one wave propagation characteristic that is substantially similar to the resonating body.

* * * * *